(12) United States Patent
Imig et al.

(10) Patent No.: US 11,358,968 B2
(45) Date of Patent: Jun. 14, 2022

(54) SUBSTITUTED EPOXYEICOSATRIENOIC ACID (EET) ANALOGS FOR TREATMENT OF KIDNEY DISEASE

(71) Applicant: THE MEDICAL COLLEGE OF WISCONSIN, INC., Milwaukee, WI (US)

(72) Inventors: John D. Imig, Pewaukee, WI (US); John R. Falck, University Park, TX (US); Abdul Hye Khan, Milwaukee, WI (US); Adeniyi Adebesin, Dallas, TX (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 0 days.

(21) Appl. No.: 16/647,603

(22) PCT Filed: Sep. 14, 2018

(86) PCT No.: PCT/US2018/051132
§ 371 (c)(1),
(2) Date: Mar. 16, 2020

(87) PCT Pub. No.: WO2019/055814
PCT Pub. Date: Mar. 21, 2019

(65) Prior Publication Data
US 2020/0255433 A1 Aug. 13, 2020

Related U.S. Application Data

(60) Provisional application No. 62/559,355, filed on Sep. 15, 2017.

(51) Int. Cl.
*A61K 31/4985* (2006.01)
*C07D 487/04* (2006.01)
*A61P 13/12* (2006.01)
*C07D 519/00* (2006.01)

(52) U.S. Cl.
CPC ............ *C07D 487/04* (2013.01); *A61P 13/12* (2018.01); *C07D 519/00* (2013.01)

(58) Field of Classification Search
CPC .................................................. A61K 31/4985
USPC ........................................................ 514/249
See application file for complete search history.

(56) References Cited

U.S. PATENT DOCUMENTS

| 9,127,027 | B2 | 9/2015 | Imig |
| 9,422,318 | B2 | 8/2016 | Imig |
| 2012/0177593 | A1 | 7/2012 | Baker, Jr. |
| 2014/0234278 | A1 | 8/2014 | Heffner et al. |

FOREIGN PATENT DOCUMENTS

| WO | 2012138706 A1 | 10/2012 | |
| WO | WO-2019055814 A2 * | 3/2019 | ............ A61K 47/551 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Bonaterra, GA, et al. "Cytoprotection by omega-3 fatty acids as a therapeutic drug vehicle when combined with nephrotoxic drugs in an intravenous emulsion: Effects on intraglomerular mesangial cells." Toxicology reports 1 (2014):843-857.
Bongers M.L., et al. (2012) Cost effectiveness of treatment with new agents in advanced non-small-cell lung cancer: a systematic review. Pharmacoeconomics 30, 17-34.
Capdevila, J. H., et al. "The Cyp2c44 epoxygenase regulates epithelial sodium channel activity and the blood pressure responses to increased dietary salt." Journal of Biological Chemistry 289.7 (2014): 4377-4386.
Imig, J.D. (2012) Epoxides and soluble epoxide hydrolase in cardiovascular physiology. Physiol. Rev. 92, 101-130.
Imig, J.D. et al. "A Kidney Targeted Epoxyeicosatrienoic Acid Analog, EET-F01, Reduces Cisplatin-induced Nephrotoxicity." Hypertension 70 suppl_1 (2017): A111-A111. Presentation abstract orignally published Sep. 14, 2017.
Imig, J.D. et al. (2009) Soluble epoxide hydrolase as a therapeutic target for cardiovascular diseases. Nat. Rev. Drug Discov. 8, 794-805.
International Searching Authority, International Search Report and Written Opinion for application PCT/US2018/051132, dated Feb. 27, 2019.
Jichova, S, et al. "Epoxyeicosatrienoic acid analog attenuates the development of malignant hypertension, but does not reverse it once established: a study in Cyp1a1-Ren-2 transgenic rats." Journal of hypertension 34.10 (2016): 2008.
Khan Mah, et al. (2013) Novel orally active epoxyeicosatrienoic acid (EET) analogs attenuate cisplatin nephrotoxicity. FASEB J. 7(8), 2946-56.

(Continued)

*Primary Examiner* — Douglas M Willis
(74) *Attorney, Agent, or Firm* — Quarles & Brady LLP

(57) ABSTRACT

Described here are EET analogs conjugated to folate receptor ligands such as folic acid or folic acid analogs recognized by and selectively bound by folate receptors and other folate binding proteins and the use of such conjugated EET analogs for targeted delivery of therapeutic agents to folate-receptor bearing cell populations. More particularly, provided herein are EET analogs conjugated to folate receptor ligands and uses of such conjugated EET analogs as kidney targeted therapeutics.

9 Claims, 4 Drawing Sheets

(56) References Cited

OTHER PUBLICATIONS

Khan Mah, et al. (2013) Orally active epoxyeicosatrienoic acid analog attenuates kidney injury in hypertensive Dahl salt-sensitive rat. Hypertension. 62(5), 905-13.

Khan Mah, et al. (2014) "Epoxyeicosatrienoic acid analogue lowers blood pressure through vasodilation and sodium channel inhibition." Clinical Science 127.7. 463-474.

Khan Mah, et al. (2014) Epoxyeicosatrienoic acid analog attenuates angiotensin II hypertension and kidney injury. Front Pharmacol. 5, 216.

Khan Mah, et al. (2016) Epoxyeicosatrienoic acid analogue mitigates kidney injury in a rat model of radiation nephropathy. Clin Sci (Lond). 30(8), 587-99.

Kintzel P.E. (2001) Anticancer drug-induced kidney disorders. Drug Saf. 24, 19-38.

Levy A.R., et al. (2011) Indirect comparison of the efficacy of cetuximab and cisplatin in squamous cell carcinoma of the head and neck. Curr. Med. Res. Opin. 27, 2253-2259.

Miller R.P., et al. (2010) Mechanisms of Cisplatin nephrotoxicity. Toxins 2, 2490-2518.

Perazella M.A., et al. (2010) Nephrotoxicity from chemotherapeutic agents: clinical manifestations, pathobiology, and prevention/therapy. Semin. Nephrol. 30, 570-581.

Sánchez-González P.D., et al. (2011) An integrative view of the pathophysiological events leading to cisplatin nephrotoxicity. Crit. Rev. Toxicol. 41, 803-821.

Wang D., et al. (2005) Cellular processing of platinum anticancer drugs. Nat. Rev. Drug Discov. 4, 307-320.

International Searching Authority, International Search Report and Written Opinion for application PCT/US2012/032090, dated Jul. 25, 2012.

Falck et al: "14,15-Epoxyeicosa-5,8,11-trieonoic Acid (14,15-EET) Surrogates Containing Epoxide Bioisosteres: Influence upon Vascular Relaxation and Soluble Exposide Hydrolase Inhibition", Jnl of Med. Chem., Amer. Chem Society, US; vol. 52, No. 16; Aug. 27, 2009; pp. 5069-5075.

Parrish et al: "Attenuation of cisplatin nephrotoxicity by inhibition of soluble eopxide hydrolase", Cell. Biol. Toxicol., vol. 25, 2007, pp. 217-225.

* cited by examiner

EET-F01 Decreases Cisplatin-induced Renal Injury

SUBSTITUTED EPOXYEICOSATRIENOIC ACID (EET) ANALOGS FOR TREATMENT OF KIDNEY DISEASE

CROSS-REFERENCE TO RELATED APPLICATIONS

This application represents the national stage entry of PCT International Application No. PCT/US2018/051132, filed on Sep. 14, 2018, and claims priority to U.S. Provisional Patent Application No. 62/559,355, filed Sep. 15, 2017, each of which is incorporated herein by reference as if set forth in its entirety.

STATEMENT REGARDING FEDERALLY SPONSORED RESEARCH

N/A

BACKGROUND

According to the National Kidney Foundation, 10% of the population worldwide is affected by chronic kidney disease (CKD), and millions die each year because they do not have access to affordable or effective treatment. With the increasing prevalence of CKD and end-stage renal disease (ESRD), the economic burden of CKD is a growing concern to patients, their caregivers, and payers. Significant health care costs are incurred to manage the clinical complexities of CKD and ESRD patients, including costs associated with the detection and management of CKD, ESRD treatment, and simultaneous management of comorbid conditions such as diabetes, hypertension, and congestive heart failure. Progressive organ damage associated with renal and cardiovascular diseases is a major cause of morbidity and mortality. Hypertension and diabetes are the two main diseases responsible for the increase in ESRD and the number of patients on dialysis. Despite increased awareness of Chronic Kidney Disease (CKD) as a significant worldwide medical problem, there remain few pharmacological therapies available to prevent or slow the progression of CKD to End Stage Renal Disease (ESRD), much less therapies that result in a cure.

Drug-induced nephrotoxicity is also a problem for patients receiving platinum-based chemotherapy agents for treatment of a variety of malignancies. For example, cisplatin is an effective chemotherapeutic agent, but several adverse side effects are associated with the use of cisplatin in clinical practice. The most common adverse effect for patients receiving cisplatin is severe nephrotoxicity which occurs in 25-40% of cisplatin treated patients. It is widely acknowledged that there is a need to develop agent that could protect the kidney from the adverse effect of cisplatin during its clinical use.

DETAILED DESCRIPTION

All publications, including but not limited to patents and patent applications, cited in this specification are herein incorporated by reference as though set forth in their entirety in the present application.

Described here and in the following pages are kidney targeted epoxyeicosatrienoic acid (EET) analogs and methods of using such EET analogs for the treatment of renal and cardiovascular diseases. More particularly, provided herein are EET analogs conjugated to folate receptor ligands such as folic acid or folic acid analogs recognized by and selectively bound by folate receptors and other folate binding proteins and uses of such conjugated EET analogs as kidney targeted therapeutics. In general, these compounds and methods are based at least in part on the inventor's development of EET agonists and analogs having promising therapeutic potential for cardiovascular and kidney diseases. The inventors previously synthesized a series of analogs of 14,15-EET, defined the basic pharmacophore and stabilized it from metabolic inactivation. A subset of these analogs, named EET-A, EET-B and EET-C22, are orally active with good pharmacokinetic properties. See, e.g., PCT/US2012/032090 and U.S. Pat. Nos. 9,422,318 and 9,127,027, each of which is incorporated herein by reference as if set forth in its entirety.

In a first aspect, provided herein is a kidney-targeted analog of epoxyeicosatrienoic acid (EET) comprising an EET analog conjugated to folic acid (also known as folate) receptor ligand such as folic acid, methotrexate, or a folate analog that binds to the folate receptor. Without being bound to any particular theory or mechanism of action, it is believed that linkage of a folate receptor ligand to an EET analog targets the folate-linked compound to cells expressing high levels of folate receptors (FR) such as proximal tubular cells of the kidney. Suitable folate receptor ligands include folic acid, methotrexate, and folate analogs that bind to the folate receptor. The folate receptor ligand may be directly conjugated to the EET analog, or alternatively, the folate receptor ligand may be indirectly conjugated to the EET analog by a linker.

In some cases, the EET analog used to form the conjugated compound is selected from the group consisting of

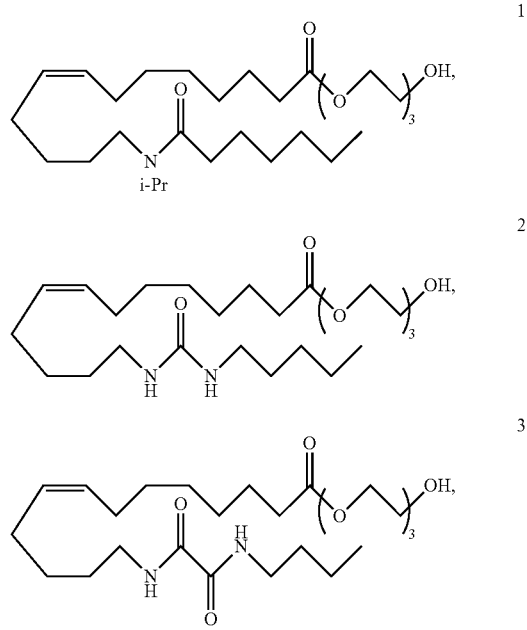

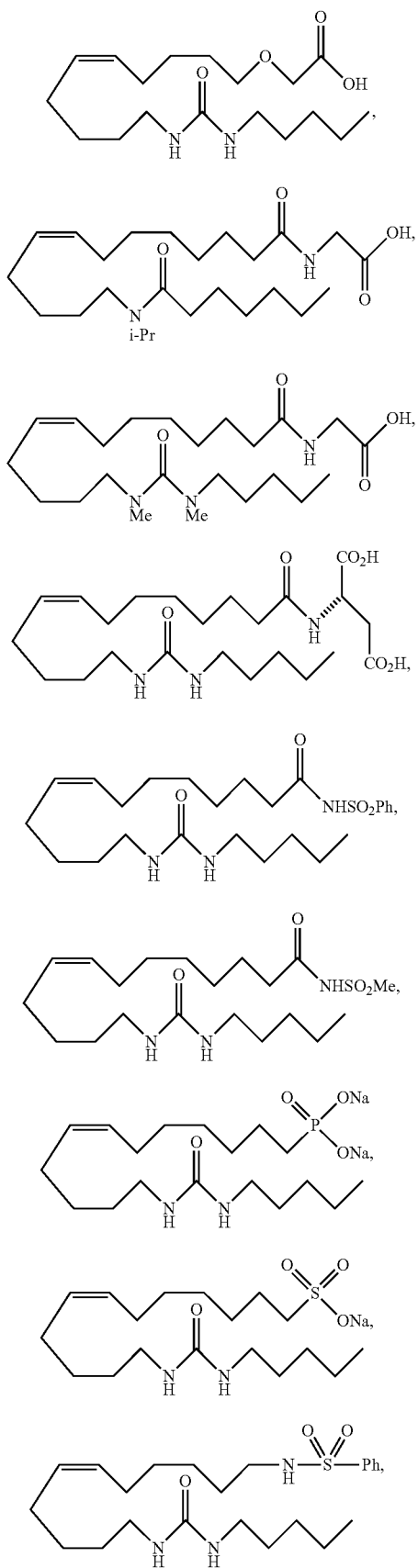
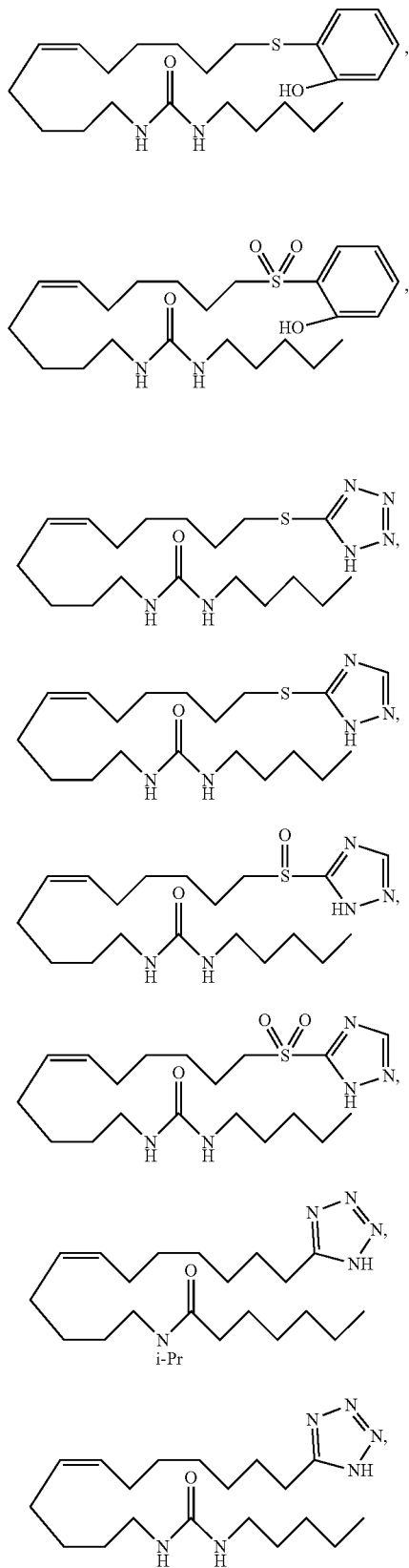

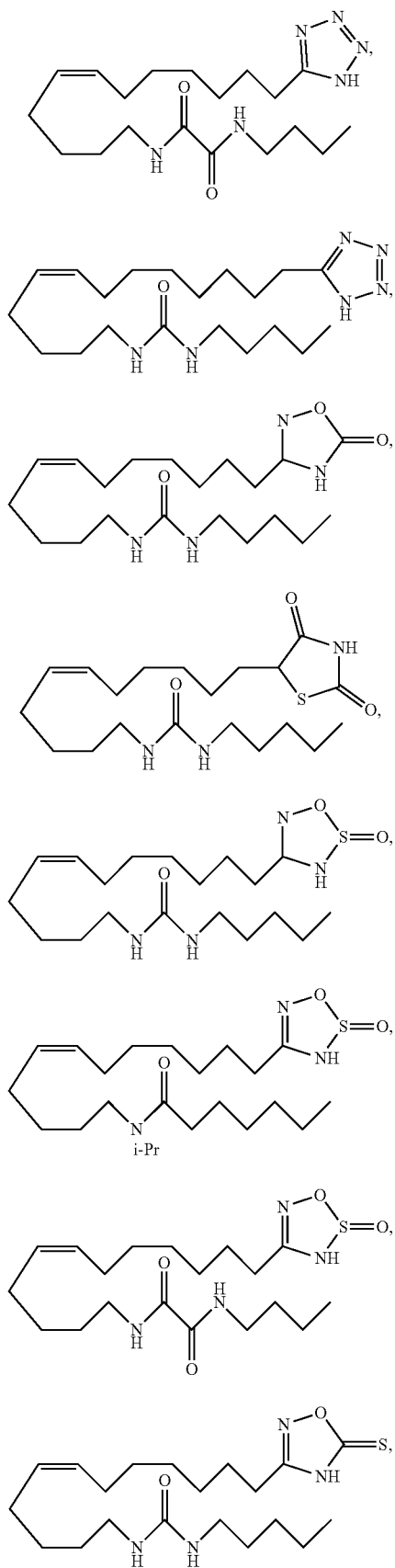
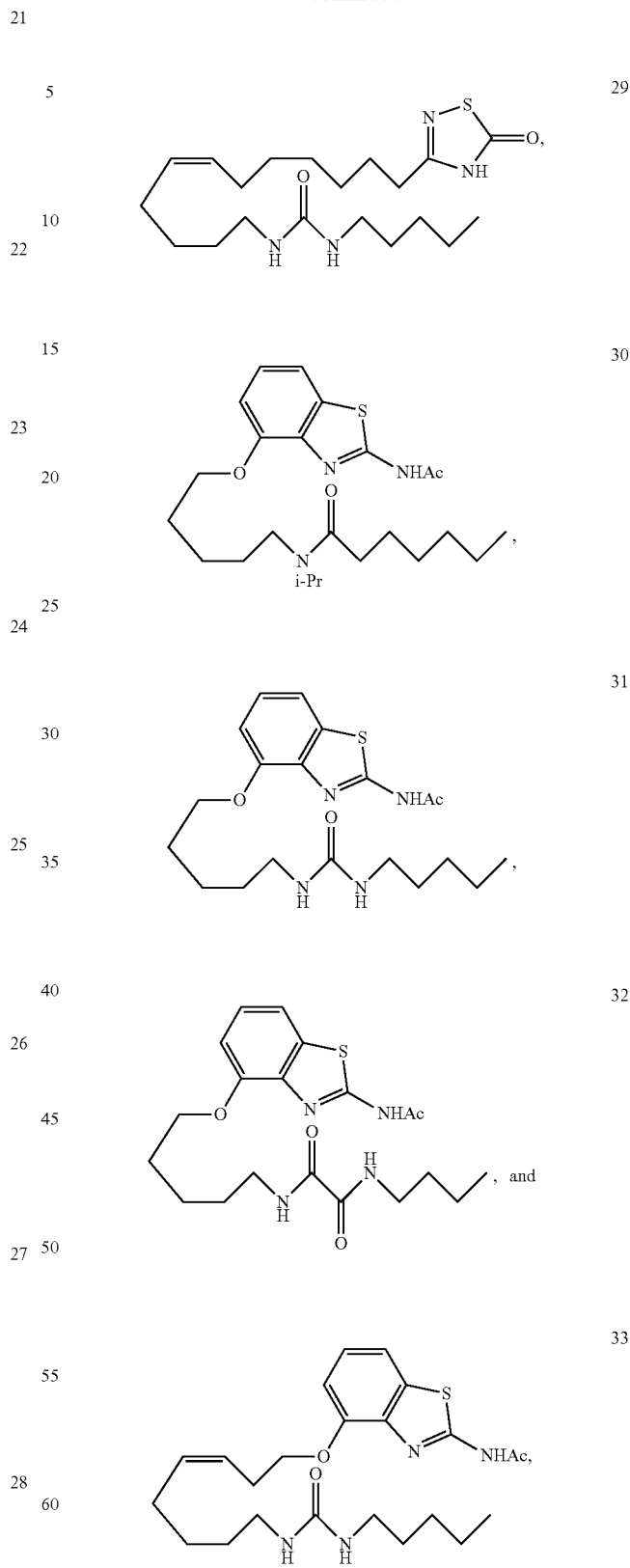
In certain embodiments, the compound of the invention having the following formula and further exhibits binding affinity for a folate receptor:

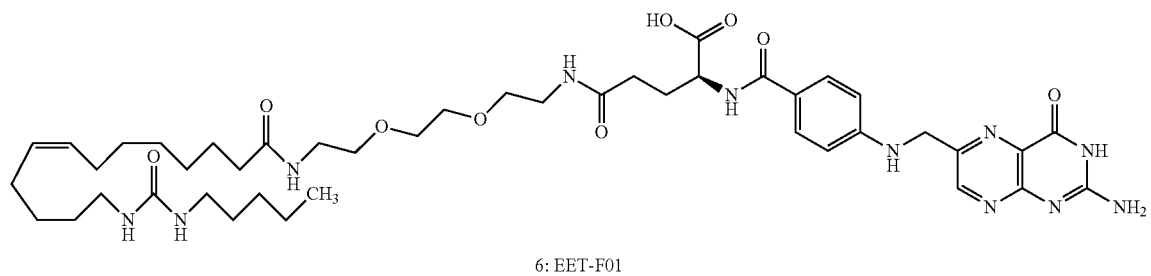 [SMILES: CCCCCNC(=O)NCCCC/C=C\CCCCCCC(=O)NCCOCCOCCNC(=O)CC[C@H](NC(=O)c1ccc(NCc2cnc3nc(N)[nH]c(=O)c3n2)cc1)C(=O)O]

6: EET-F01

Figure 4:
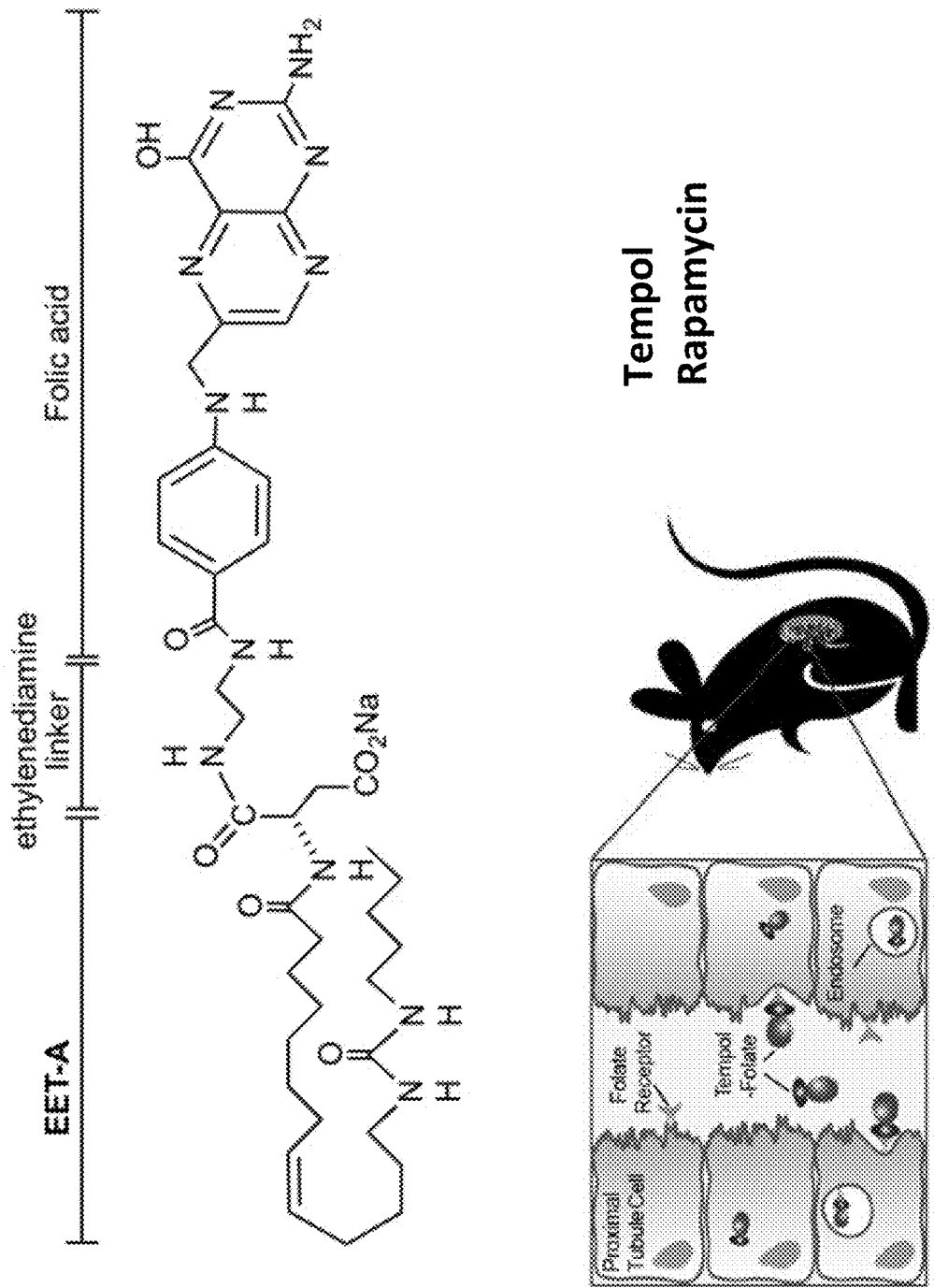
FIG. 4 illustrates an embodiment of a folate-conjugated EET analog.

Linkers and linking chemistry appropriate for folate-conjugation of EET analogs for synthesis of kidney-targeted EET analogs include, without limitation, Polyethylene glycol (PEG) linkers, PEG-diamine linkers. For example, in certain embodiments, the EET analog is conjugated to a folate receptor ligand via a PEG diamine linker. In other cases, the linker comprises ethylenediamine (see, for example, FIG. 4), diisocyanate, diisothiocynate, carbodiimide, bis(hydroxysuccinimide) ester, maleimide-hydroxysuccinimide ester, glutaraldehyde, or a combination thereof.

The linker may create either a permanent or a semipermanent (i.e., labile) linkage. The inclusion of a semipermanent linkage is especially advantageous for applications in which cellular uptake of the drug is desired.

Synthesis of kidney targeted EET analogs may be accomplished according to the following illustrative synthesis protocols. Synthesis of other folic acid analogs may be accomplished by methods known to the skilled artisan. In addition, the optional incorporation of a linker may also be accomplished by methods known to the skilled artisan.

Synthesis of Folate-Conjugates

Synthesis of EET-F01:

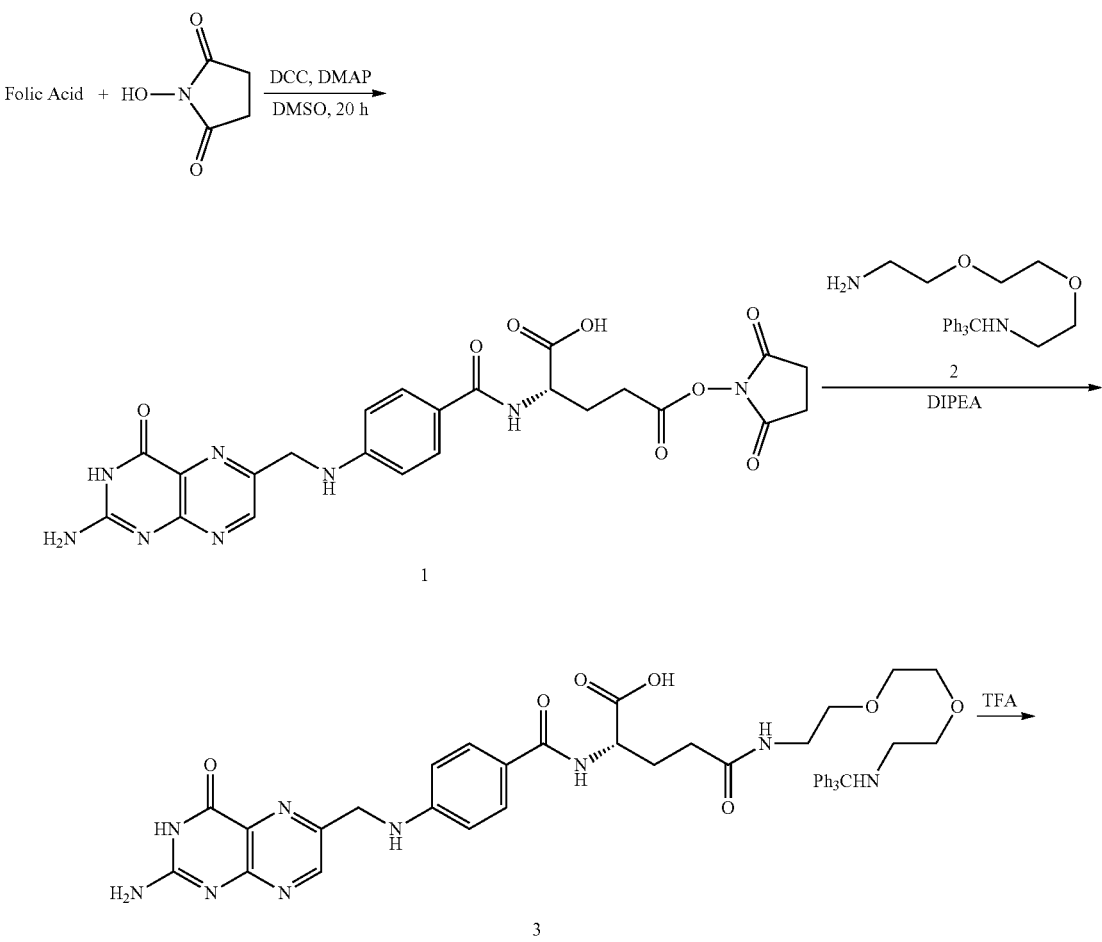

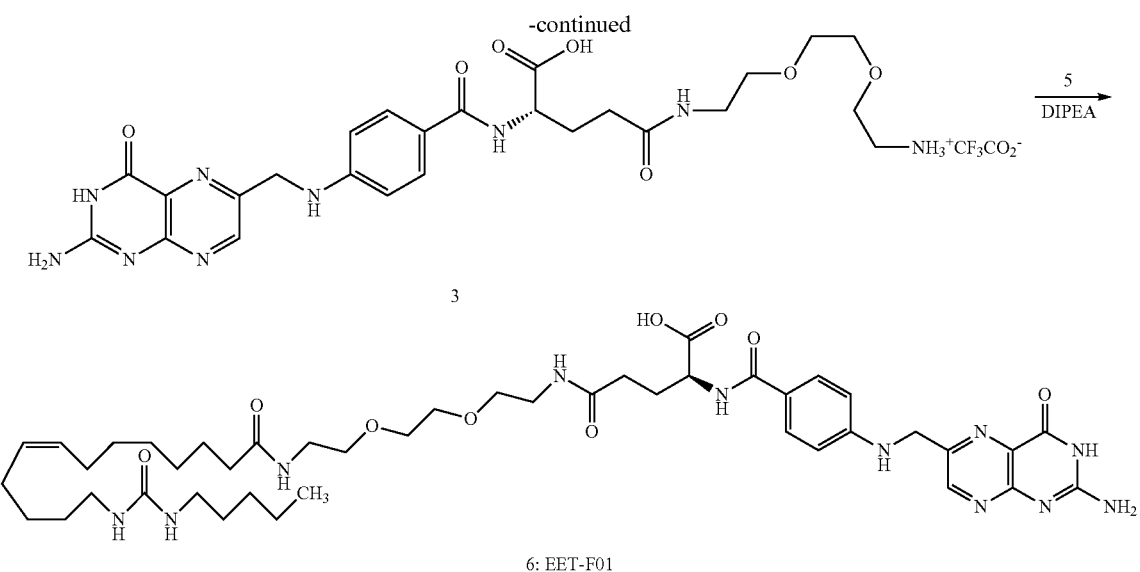

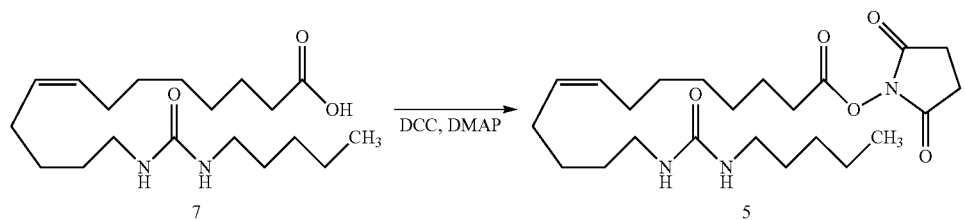 [SMILES: CCCCCNC(=O)NCCCC/C=C\CCCCCCC(=O)O ; CCCCCNC(=O)NCCCC/C=C\CCCCCCC(=O)ON1C(=O)CCC1=O]

Experimental:

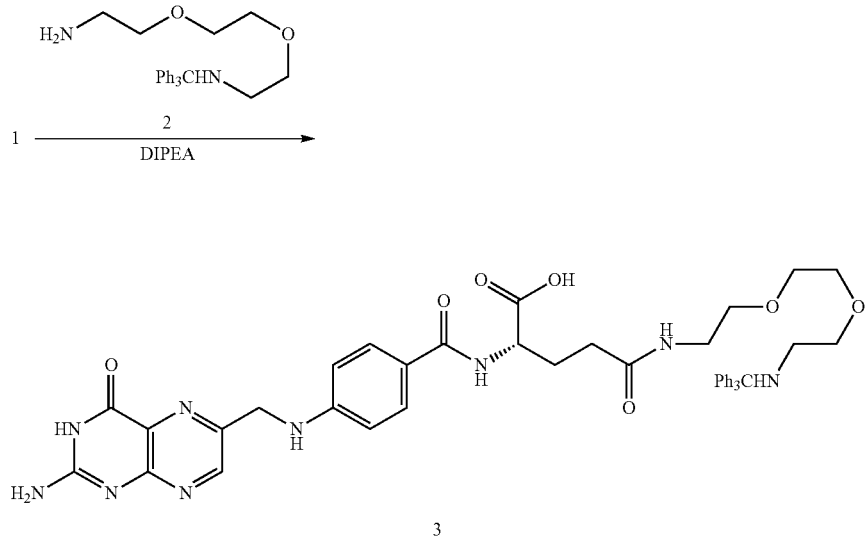

Diisopropylethylamine (DIPEA, 1.18 mL, 6.78 mmol, 3.00 equiv) was added to a mixture of N-hydroxysuccinimide (NHS) folate ester[1] (1) (11.44 g, 2.26 mmol) and 2-12-(2-aminoethoxy)ethoxyl-N-tritylethan-1-amine[2] (2) (1.06 g, 2.71 mmol, 1.20 equiv) in anhydrous DMSO (20 mL). After 18 h, the DMSO was evaporated (50° C., 0.1 torr) and the residue was triturated with acetone/ether (20/70, 2×50 mL) and then acetone (2×50 mL). The residue was dried on high vacuum overnight to give an orange solid (orange solid, 2.00 g) which was carried on to the next step without further purification.

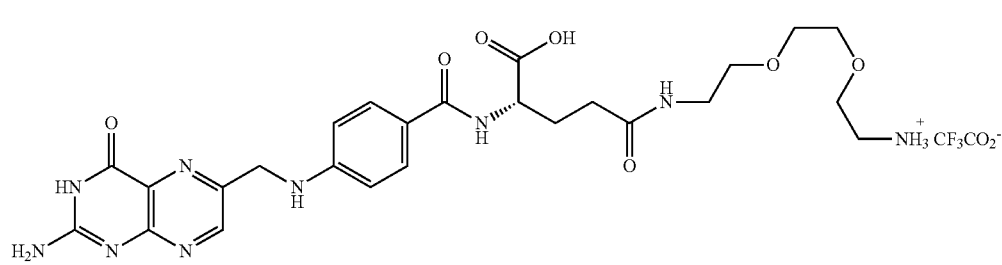

4

Trifluoroacetic acid (TFA, 5.36 mL) was added dropwise to a suspension of crude 3 (1.09 g, 1.34 mmol) in CH$_2$Cl$_2$/H$_2$O (5/1, 6 mL). After gently shaking for 2 h, the mixture was concentrated in vacuo and the residue was azeotropically dried with dry toluene (10 mL). The residue was triturated with CH$_2$Cl$_2$ (5×5 mL); the yellowish CH$_2$Cl$_2$ supernatant was removed each time with a pipette and gradually became less yellow with each wash until nearly colorless. The crude 4 (thick red oil) was used in the next step without further purification.

Hz, 2H), 5.79-5.69 (m, 2H), 5.38-5.28 (m, 2H), 4.49 (d, J=6.1 Hz, 2H), 3.52-3.45 (m, 4H), 3.22-3.13 (m, 4H), 3.01-2.87 (m, 4H), 2.10-2.09 (m, 2H), 2.05 (t, J=7.5 Hz, 2H), 2.01-1.93 (m, 4H), 1.51-1.40 (m, 2H), 1.40-1.14 (m, 18H), 0.86 (t, J=7.0 Hz, 3H). LCMS (ES-APCI$^+$) Calcd. for [C$_{44}$H$_{67}$N$_{11}$O$_9$]$^+$894.1, Found 894.4.

Synthesis of NHS EET analog ester 5. .N-Hydroxysuccinimide (NHS, 0.165 g, 1.43 mmol, 1.10 equiv) and dicy-

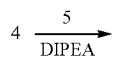

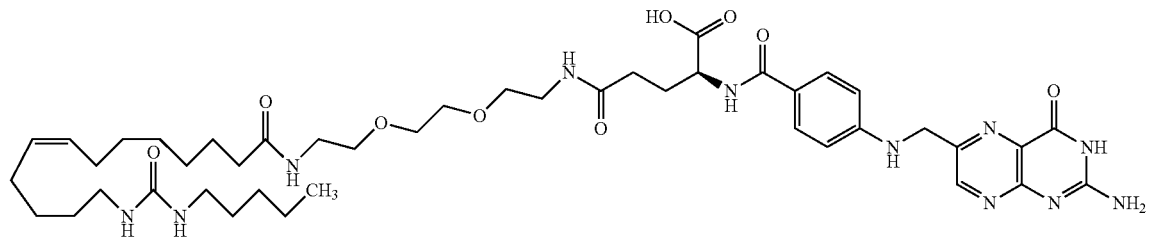

6: EET-F01

DIPEA (1.13 mL, 6.50 mmol, 5.00 equiv) was added dropwise to a suspension of crude 4 (0.891 g, 1.30 mmol) in anhydrous DMSO (6 mL). After 15 min, a solution of NHS EET analog ester 5 (0.569 g, 1.30 mmol) in dry CH$_2$Cl$_2$ (6 mL) was added. After 24 h, the reaction mixture was diluted with ice-cold 20% acetone/Et$_2$O (50 mL). The supernatant was decanted away from the resulting precipitate and the residue was triturated sequentially with additional 20% acetone/Et$_2$O (50 mL), 50% acetone/Et$_2$O (100 mL), 0.1 N HCl (20 mL), and then acetone (2×50 mL). The residue was dried under high vacuum overnight to give EET-F01 (6) as an orange solid (0.690 g, 59%).

$^1$H NMR (500 MHz, DMSO-d$_6$) δ 8.65 (s, 1H), 7.93-7.80 (m, 1H), 7.73-7.58 (m, 2H), 6.95 (s, 1H), 6.64 (dd, J=8.7, 2.3 clohexylcarbodiimide (DCC, 0.322 g, 1.56 mmol, 1.20 equiv) were added to a stirring 0° C. solution of EET analog$^3$ 7 (0.443 g, 1.30 mmol) in dry EtOAc (26 mL). After 5 min, N,N-dimethylpyridine (DMAP, 15.9 mg, 0.13 mmol, 0.100 equiv) was added and the suspension was warmed to rt. After 24 h, the reaction was filtered through a pad of Celite™ and the Celite™ bed was washed with EtOAc. The filtrate was washed with saturated aq. NaHCO$_3$ (10 mL) and brine (10 mL). The organic layer was dried over Na$_2$SO$_4$, filtered, and concentrated in vacuo to give crude 5 which was used in the next step without further purification.

Synthesis of EET-A Folate Conjugate:

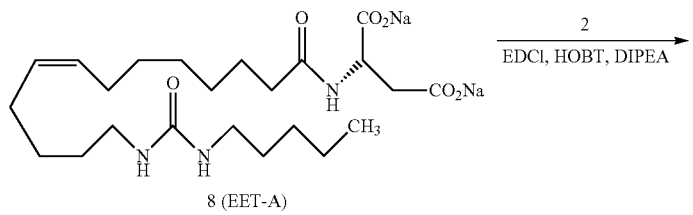

8 (EET-A)

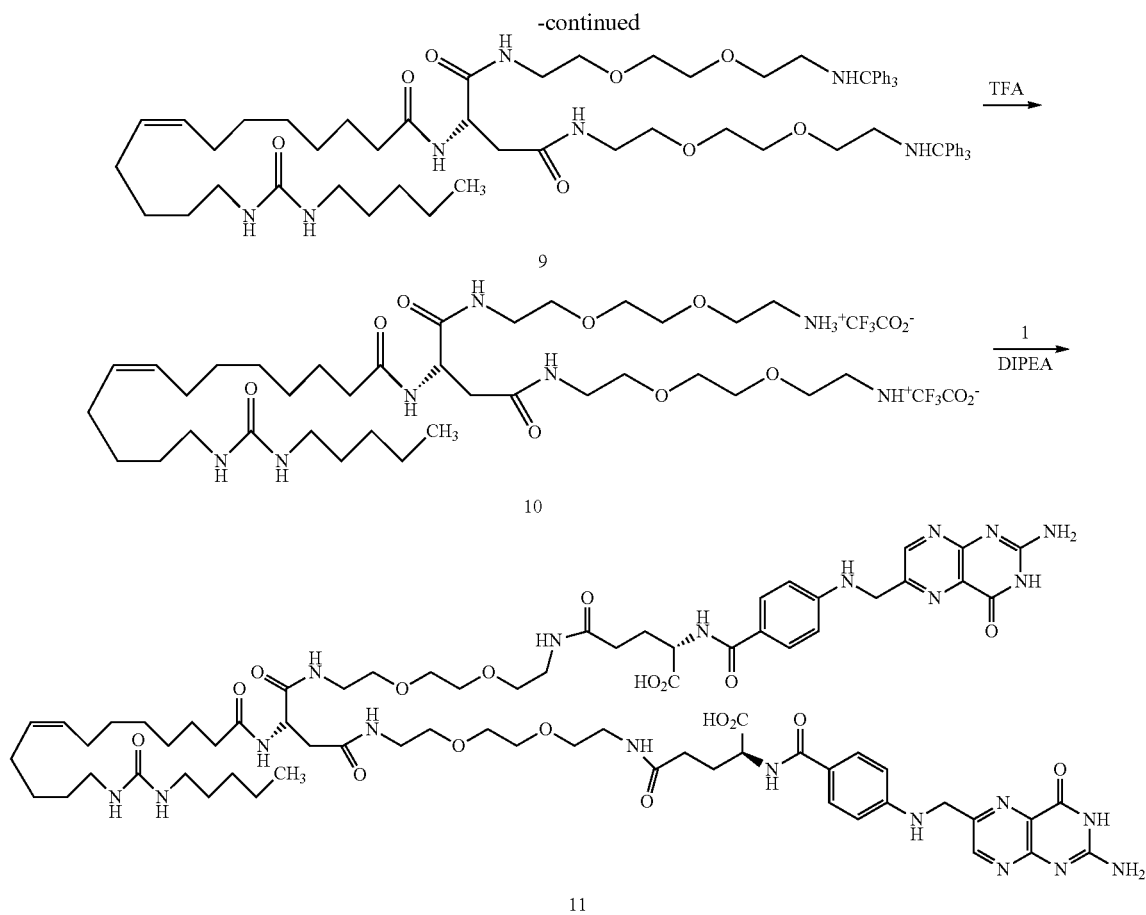

Synthesis of 9. A mixture of EET-A disodium salt[3] (100 mg, 0.20 mmol), N-(3-dimethylaminopropyl)-N'-ethylcarbodiimide hydrochloride (EDCI.HCl, 88 mg, 0.460 mmol, 2.3 equiv), and hydroxybenzotriazole (HOBt, 6.10 mg, 0.04 mmol, 0.2 equiv) in anhydrous DMF (1 mL) was stirred at rt. After 2 h, 2 (188 mg, 0.481 mmol, 2.40 equiv) in dry $CH_2Cl_2$ (1 mL) and DIPEA (79 µL, 0.440 mmol, 2.20 equiv) were added sequential. Following an additional 40 h, the mixture was diluted with MeOH (10 mL) and concentrated in vacuo. The crude product was purified using a Teledyne Isco Combiflash® $R_f$ chromatographic system (4 g $SiO_2$ column) eluted with a gradient of 0-100% EtOAc/hexane over 25 min; 100% EtOAc for 15 min; and 10% MeOH/$CH_2Cl_2$ for 7 min to give 9 (169 mg, 70%).

$^1$H NMR (500 MHz, $CD_3OD$) δ 7.51-7.44 (m, 14H), 7.33-7.25 (m, 14H), 7.24-7.17 (m, 6H), 5.87 (s, 1H), 5.40-5.33 (m, 2H), 4.69 (dd, J=7.5, 5.9 Hz, 1H), 3.71-3.49 (m, 18H), 3.17-3.07 (m, 4H), 2.62 (dd, J=15.0, 6.0 Hz, 1H), 2.53 (dd, J=15.0, 7.7 Hz, 1H), 2.35 (t, J=5.5 Hz, 4H), 2.21 (t, J=7.6 Hz, 3H), 2.13-1.99 (m, 4H), 1.66-1.54 (m, 2H), 1.53-1.45 (m, 4H), 1.43-1.26 (m, 14H), 0.93 (t, J=6.9 Hz, 3H).

Synthesis of 10. Trifluoroacetic acid (TFA, 0.40 mL) was added dropwise to a mixture of trityl-protected amine 9 (130 mg, 0.108 mmol) in $H_2O$ (0.50 mL) and $CHCl_3$ (1.5 mL). After 45 min, the reaction was diluted with MeOH (3 mL) and concentrated in vacuo. Co-evaporation with toluene (3×5 mL) gave 10 as a white solid which was taken to the next step without further purification.

Synthesis of 11. DIPEA (77 µL, 0.432 mmol, 4 equiv) was added to a mixture of crude 1 (116 mg, 0,216 mmol, 2 equiv) and 10 (77 mg, 0.108 mmol) in anhydrous DMSO (1.50 mL). After 40 h, the mixture was poured with stirring into 0° C. $Et_2O$ (25 mL). The supernatant was carefully decanted from the resulting precipitate and the precipitate was triturated with acetone/$Et_2O$ (30/70, 30 mL) and acetone/$CH_2Cl_2$ (30/70, 30 mL). The residue was dried under high vacuum to give 11 (57 mg) as an orange solid.

$^1$H NMR (500 MHz, DMSO-$d_6$) δ 8.73-8.61 (m, 2H), 8.12-7.83 (m, 4H), 7.76-7.55 (m, 3H), 7.03-6.88 (m, 2H), 6.64 (dd, J=7.8, 4.5 Hz, 4H), 5.76 (br s, 2H), 5.40-5.20 (m, 2H), 4.57-4.42 (m, 5H), 3.68-3.44 (m, 14H), 3.22-3.08 (m, 6H), 3.06-2.88 (m, 6H), 2.02-1.84 (m, 7H), 1.53-1.14 (m, 18H), 0.92-0.78 (m, 3H).

The kidney-targeted EET analogs described herein may be formulated with a pharmaceutically acceptable carrier or excipient to form a primary therapeutic agent. "A pharmaceutically acceptable carrier" is a material that can be used as a vehicle for administering a therapeutic or prophylactic agent, (e.g., kidney-targeted EET analog), because the material is inert or otherwise medically acceptable, as well as compatible with the agent.

Also disclosed are kits that include the conjugates and/or complexes together with a pharmaceutically acceptable excipient to form a therapeutic agent. The kit may include an implement for administering the therapeutic agent. In addition, the kit may include one or more supplemental therapeutic agents and/or diagnostic agents.

Advantageous properties of kidney targeted EET analogs as described herein also include: targeted delivery of EET analogs to the kidneys, therefore leveraging the useful biological properties of EETs (e.g., vasodilation, anti-inflammation, anti-apoptosis, and anti-fibrosis) in a targeted manner; utility as a prophylactic to prevent or limit nephrotoxicity as well as an interventional therapy; effective at ten-fold lower doses than untargeted EET counterparts; and fewer systemic side effects.

In another aspect, provided herein are methods of treating kidney disease in a subject in need thereof with a compound as described herein. Also provided herein are methods for delivering a therapeutic agent to a target cell population comprising a folate receptor, the method comprising providing the compound of claim 1 and contacting the target cell population with an effective amount of the compound to permit binding of the compound to the folate receptor.

Therapeutic and preventative applications of the kidney-targeted EET analogs described herein include, without limitation, treatment of kidney diseases that begin at the proximal tubules, acute tubular necrosis (ATN), and ischemic renal injury following bypass or transplant surgery; treating or preventing drug-induced nephrotoxicity, including Cisplatin-induced nephrotoxicity; use as a preservative to store kidneys to be transplanted; treatment of diabetic nephropathy, Focal Segmental Glomerulosclerosis (FSGS), and Chronic Kidney Disease (CKD). Other therapeutic and prophylactic applications of the kidney targeted EET analogs provided herein include treatment of and/or protection from drug- and radiation-induced kidney damage, hypertension and cardiorenal syndrome kidney damage, and metabolic syndrome and diabetes nephropathy.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, preferred methods and materials are described herein.

The following Example is illustrative of certain embodiments of the invention. The examples, methods, and conditions presented therein are not to be construed as limiting the scope nor the spirit of the invention.

EXAMPLES

Example 1—Kidney-Targeted Delivery of EET Analogs

Epoxyeicosatrienoic acid (EET) analogs have exceptional therapeutic potential to combat cardiovascular and kidney diseases. EET analogs combat damage in acute and chronic kidney disease models. Biological actions attributed to EET analogs such as vasodilation, anti-inflammation, anti-apoptosis, and anti-fibrosis are ideally suited to treat kidney diseases. Although EET analogs have performed well in several in vivo models, targeted delivery of EET analogs to the kidney can be reasonably expected to reduce the level of drug needed to achieve a therapeutic effect in the kidney and obviate possible side effects.

For EET analog kidney-targeted delivery, we conjugated an EET analog to folic acid because there is a high concentration of folate receptors in renal tissue. The EET analog was conjugated to folic acid via a PEG-diamine linker. Next, we compared the kidney targeted EET analog, EET-FO1, to a well-studied EET analog, EET-A. EET-A or EET-FO1 was infused i.v. (10 mg/kg/hr) for 6 hours via the rat jugular vein. Plasma and kidney tissue were collected and EET-A or EET-FO1 measured by LC-MS-MS. EET-A plasma level was 1.6 ng/mL, but EET-A was undetectable in the kidney. On the other hand, EET-FO1 was 6.5 ng/mL in plasma and 26.7 ng/mL in kidney tissue. These data demonstrate that EET-FO1 targets the kidney. Experiments were conducted to compare EET-FO1 and EET-A to decrease cisplatin-induced nephrotoxicity. A single injection of cisplatin (7 mg/kg ip) was administered to WKY rats treated with vehicle, EET-A (10 mg/kg ip) or EET-FO1 (20 mg/kg or 2 mg/kg ip) for five days. Cisplatin increased BUN (125±11 mg/dL) and NAG (12±4 IU/L) compared to control (36±9 mg/dL and 4±1 IU/L). EET-FO1 was as effective as EET-A in decreasing BUN, NAG, and renal histological injury five days following cisplatin administration. Despite it almost 2×-greater molecular weight compared with EET-A, EET-FO1 was effective in lowering BUN and NAG at 20 mg/kg/d and at a 10-fold lower dose of 2 mg/kg/d. These data clearly demonstrate that EET-FO1 targets the kidney and allows for a lower effective dose. In conclusion, we have developed a kidney targeted EET analog, EET-FO1 that demonstrates excellent potential as a therapeutic for kidney diseases.

Example 2—Protection Against Cisplatin-Induced Nephrotoxicity Using Kidney-Targeted EET Analogs Cisplatin is a platinum-based inorganic chemotherapy agents available to treat a variety of malignancies (1-3). However, several adverse side effects are associated with the use of cisplatin in clinical practice. Among several, the most common adverse effect is severe nephrotoxicity occurs in 25-40% of cisplatin treated patients that affects the effective use of this chemotherapeutic agent (4-7). It is widely acknowledged that there is a need to develop agent that could protect the kidney from the adverse effect of cisplatin during its clinical use. One approach that can be used to develop kidney protective agent against cisplatin nephrotoxicity is targeting CYP epoxygenase pathway which produce epoxyeicosatrienoic acids (EETs) from arachidonic acids.

Several studies demonstrated that EETs display myriad of biological actions useful for organ protection, including the kidney (8,9). In these studies, we have demonstrated that synthetic EET mimetics kidney protective in numerous pathological conditions like hypertension, cisplatin nephrotoxicity and radiation nephropathy (10-14). These studies clearly demonstrated potential of EET-based approach to protect kidney in pathological situations of different etiologies and we have developed several synthetic EET analogs that have EET mimetic property.

Recently, attempts have been made to develop EET analogs that possess EET-mimetic activity along with a unique property to target the kidney. We have developed a novel form of kidney targeted EET analog by conjugating EET pharmacophore with folic acid. In preliminary studies, we investigated its ability to target kidney in compare to the EET analog without any folic acid conjugation. We also compared the ability of the folic acid conjugated EET analog with the original EET analog without any folic acid moiety in protecting the kidney against cisplatin nephrotoxicity.

Materials and Methods

All chemicals and assay kits were purchased from Sigma Aldrich (St. Louis, Mo., USA) unless and otherwise mentioned. EET analogs were designed and synthesized in the laboratory of John R. Falck, Department of Biochemistry, University of Texas Southwestern Medical Centre, Dallas, Tex.

Animal Studies: All animal studies were approved and carried out according to guidelines of the Institutional Animal Care and Use Committee, Medical College of Wisconsin. Animals were kept in a temperature-controlled environment with a 12-h light/dark cycle and were allowed free access to food and water. An acclimatization period of 6 days was allowed for the rats before experimentation.

Acute study: Overnight fasted (12-14 hrs) male SD rats (10 weeks old) were anesthetized with sodium pentobarbital (60 mg/kg, i.p.). After a tracheostomy, the left jugular vein was cannulated to continuously infuse vehicle or EET-A or folate conjugated EET analog at a rate of 6 ml/kg/hr for 6 hours. Plasma and kidney sample were collected at the end of the protocol, snap-frozen in liquid nitrogen and stored at −80° C. until analyzed for LC-MS. EET-A and folate conjugated EET analog solutions were prepared in 0.1% DMSO and 1% PEG-400 in saline.

Figure 1:
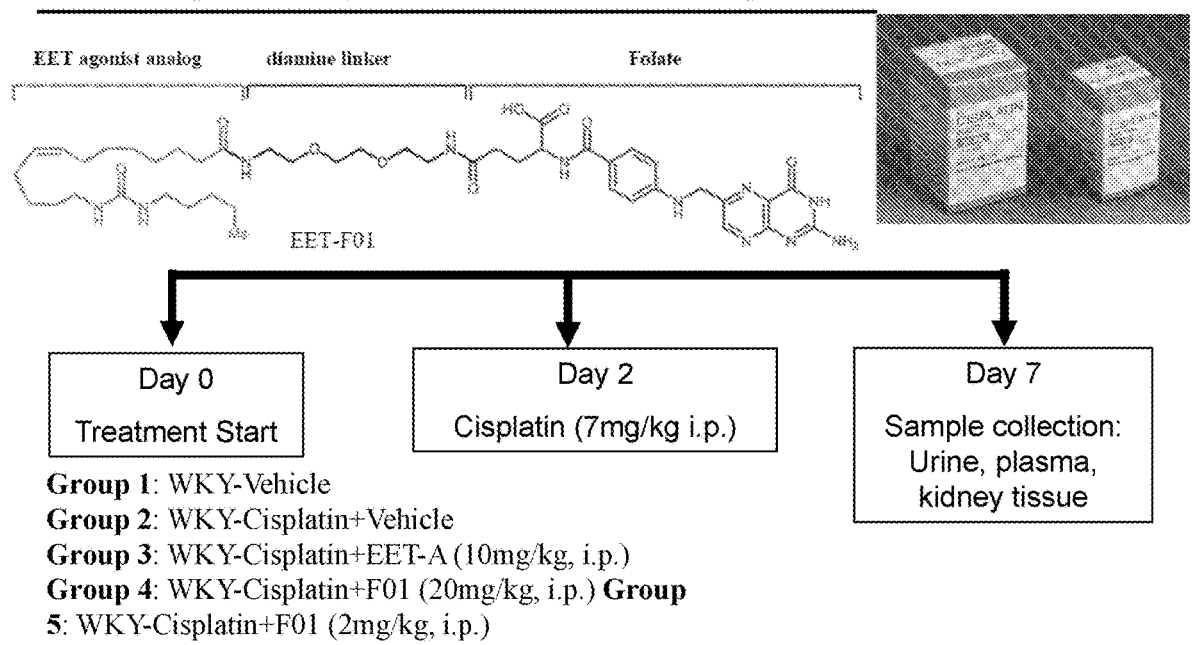
FIG. 1 is a schematic diagram of a chronic study protocol.

Chronic study: In chronic study, male Wistar-Kyoto (WKY) rats weighing 180-200 g (Charles River, Mass., USA) were used. The rats were assigned into four groups (n=4 in each group). Rats of group 1 received drinking water ad libitum and on day 7 administered DMSO (300-500 µl i.p.), which is used to prepare cisplatin solution. While, rats of groups 2,3,4&5 were pre-treated with vehicle (20% DMSO in PEG-400 v/v), EET analog (EET analog in double distilled water) or novel folate conjugated EET analog F01 at 20 mg/kg and 2 mg/kg doses (prepared in a mixture of 20% DMSO in PEG400), respectively in osmotic mini pump (2 ML, Alzet, Cupertino, CA) for seven days. On day 7 these rats were administered with a single dose of cisplatin (7 mg/kg i.p.) followed by five-days treatment vehicle, EET-A and F01. One day before euthanasia, the urine of each rat was collected over a 24-h period. Five days after cisplatin or vehicle administration, rats were anesthetized for blood sample collection followed by euthanasia. A schematic of the protocol is depicted in FIG. 1.

Biochemical analysis:The levels of blood urea nitrogen (BUN) (BioAssay Systems, Hayward, Calif., USA) and the activity of urinary N-acetyl-β-(D)-glucosaminidase (NAG) in the urine was measured by a kit from Diazyme (Diazyme Laboratories, Poway, Calif., USA).

Mass spectrometric analysis: Plasma and kidney levels of EET-A and folate conjugated EET-A were measured by LC-ESI-MS method. Samples were prepared from 200 µl of plasma or kidney homogenate from EET-A or folate conjugated EET-A treated rats using solid phase extraction with Varian Bond Elut® C18 column (Agilent Technologies, Santa Clara, Calif., USA). The extracted samples were stored at −80° C. before analysis. Samples were warmed to room temperature, dried in a stream of nitrogen and the residue reconstituted in 20 µL of acetonitrile, 124 injected. Components were resolved on a 250 mm×2.0 mm Kromasil C18-column packed with 5 µm diameter particles having 100 Å pores. Gradient elution from 80% A to 10% A was used with elutant flow of 0.2 mL/min. Solvent A was water with 0.01% formic acid and solvent B was acetonitrile with 0.01% formic acid using the following profile: 20% B to 30% B in 10 min, 30% B to 60% B in 17 min, 60% B to 90% B in 28 min, hold at 100% for 7 min, then 7 min re-equilibration. MS/MS analysis was performed on an Agilent 6460 triple quadrupole mass spectrometer equipped with a Jet Stream™ interface. Precursor ion, product ion, collision energy and fragmenter voltage were optimized for each compound in negative polarity. Other parameters were as follows: drying gas flow=10 L/min at 325° C., nebulizer=20 psi, sheath gas flow=11 L/min at 325° C., capillary=3.5 kV, and nozzle=1.0 kV. Results acquired at unit-mass resolution.

Results

Figure 2:
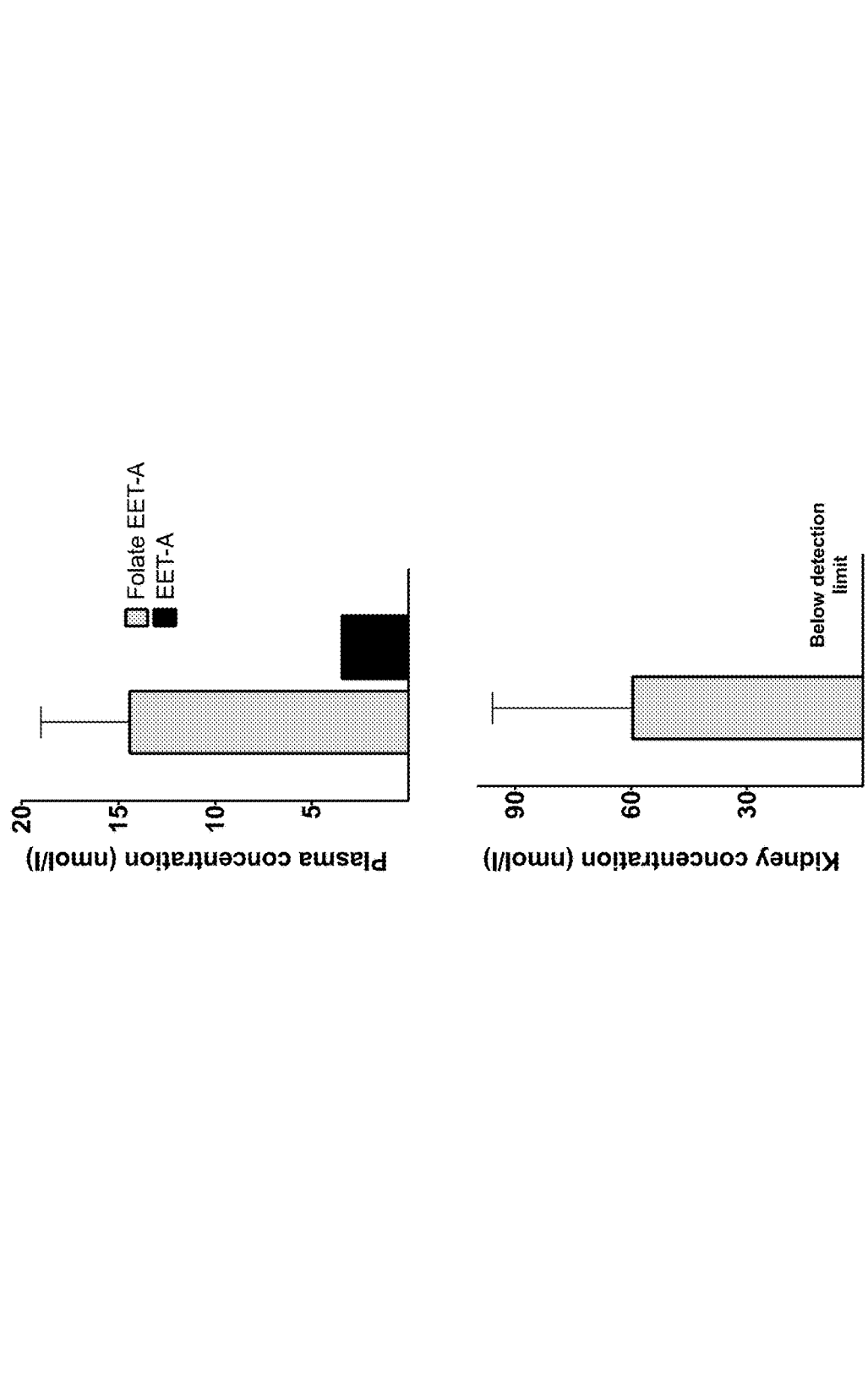
FIG. 2 demonstrates that a folate-conjugated form of an EET analog targets to the kidney.

Plasma and kidney content of F01 is higher than EET-A after acute intravenous administration In the acute animal study, equal doses of EET-A and F01 were administered intravenously for 6 hours followed by plasma and kidney tissue collection. We demonstrated 5-fold higher plasma level of F01 compared to EET-A after 6-hour continuous administration of F01 and EET-A (FIG. 2). Interestingly, we also demonstrated that after 6-hour continuous administration the kidney content of EET-A was almost un-detectable compared to F01 content in the kidney (FIG. 2).

Figure 3:
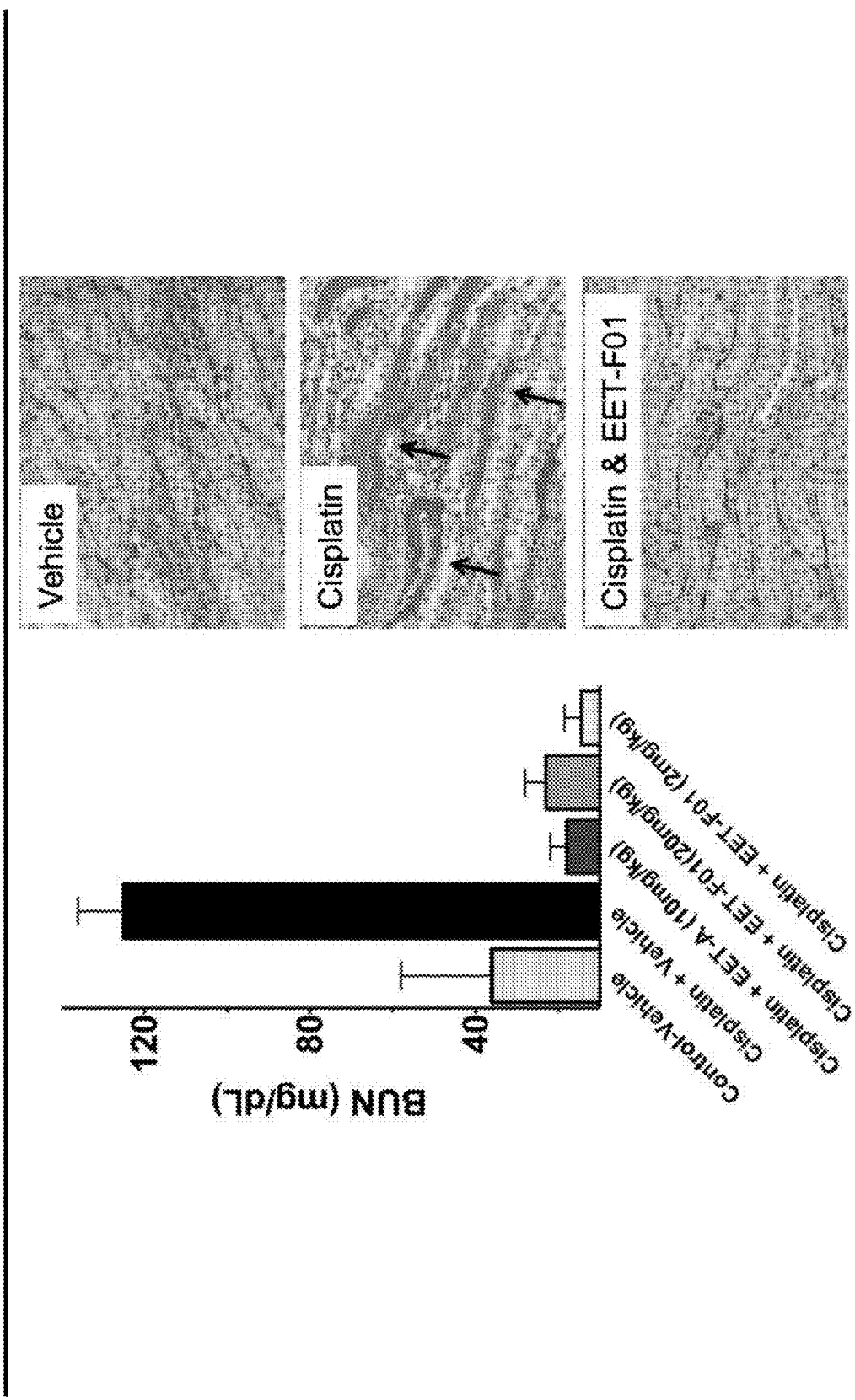
FIG. 3 demonstrates decreased cisplatin-induced renal injury using a folate conjugated form of an EET analog.

Chronic treatment of F01 demonstrated better kidney protective action than EET-A against cisplatin nephrotoxicity In a separate set of experiment groups of rats were pre-treated with F01 and EET-A before induction of cisplatin nephropathy and then further treated with the test compounds (F01 and EET-A) for another 5 days. The kidney protective actions of F01 and EET-A is determined from the level of blood urea nitrogen (BUN) and urinary content of NAG. We demonstrated a better kidney protective action of F01 compared to EET-A, the non-folate form of EET analog (FIG. 3).

Conclusion

The folate conjugated form of an EET analog, F01 has ability to reach the plasma and the kidney in a faster rate than its non-folate conjugated form. Also, the F01 compound demonstrated superior kidney protective action than EET-A against cisplatin nephrotoxicity.

REFERENCES

Bongers M. L., Coupé V. M., Jansma E. P., Smit E. F., Uyl-de Groot C. A. (2012) Cost effectiveness of treatment with new agents in advanced non-small-cell lung cancer: a systematic review. *Pharmacoeconomics* 30, 17-34.

Levy A. R., Johnston K. M., Sambrook J., Donato B., Penrod J. R., Corral M., Chasen M. (2011) Indirect comparison of the efficacy of cetuximab and cisplatin in squamous cell carcinoma of the head and neck. *Curr. Med. Res. Opin.* 27, 2253-2259.

Wang D., Lippard S. J. (2005) Cellular processing of platinum anticancer drugs. *Nat. Rev. Drug Discov.* 4, 307-320.

Kintzel P. E. (2001) Anticancer drug-induced kidney disorders. *Drug Saf* 24, 19-38.

Miller R. P., Tadagavadi R. K., Ramesh G., Reeves W. B. (2010) Mechanisms of Cisplatin nephrotoxicity. *Toxins* 2, 2490-2518.

Sánchez-González P. D., Lopez-Hernandez F. J., López-Novoa J. M., Morales A. I. (2011) An integrative view of the pathophysiological events leading to cisplatin nephrotoxicity. *Crit. Rev. Toxicol.* 41, 803-821.

Perazella M. A., Moeckel G. W. (2010) Nephrotoxicity from chemotherapeutic agents: clinical manifestations, pathobiology, and prevention/therapy. *Semin. Nephrol.* 30, 570-581.

Imig J. D. (2012) Epoxides and soluble epoxide hydrolase in cardiovascular physiology. *Physiol. Rev.* 92, 101-130.

Imig J. D., Hammock B. D. (2009) Soluble epoxide hydrolase as a therapeutic target for cardiovascular diseases. *Nat. Rev. Drug Discov.* 8, 794-805.

Khan A. H., Falck J. R., Manthati V. L., Campbell W. B., Imig J. D. (2014) Epoxyeicosatrienoic acid analog attenuates angiotensin II hypertension and kidney injury. *Front Pharmacol.* 5,216.

Khan M. A., Liu J., Kumar G., Skapek S. X., Falck J. R., Imig J. D. (2013) Novel orally active epoxyeicosatrienoic acid (EET) analogs attenuate cisplatin nephrotoxicity. *FASEB J.* 7(8), 2946-56.

Hye Khan M. A., Fish B., Wahl G., Sharma A., Falck J. R., Paudyal M. P., Moulder J. E., Imig J. D., Cohen E. P. (2016) Epoxyeicosatrienoic acid analogue mitigates kidney injury in a rat model of radiation nephropathy. *Clin Sci (Load).* 30(8), 587-99.

Hye Khan M. A., Neckár J., Manthati V., Errabelli R., Pavlov T. S., Staruschenko A., Falck J. R., Imig J. D. (2013) Orally active epoxyeicosatrienoic acid analog attenuates kidney injury in hypertensive Dahl salt-sensitive rat. *Hypertension.* 62(5), 905-13.

The present invention has been described in terms of one or more preferred embodiments, and it should be appreciated that many equivalents, alternatives, variations, and modifications, aside from those expressly stated, are possible and within the scope of the invention.

We claim:

1. A compound having the formula:

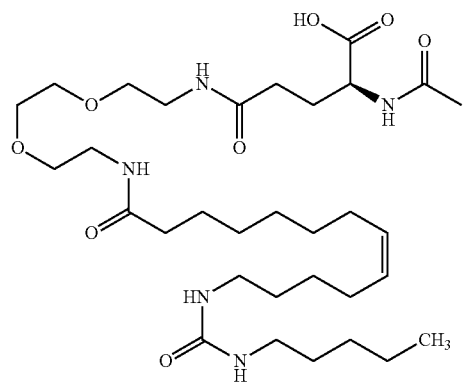

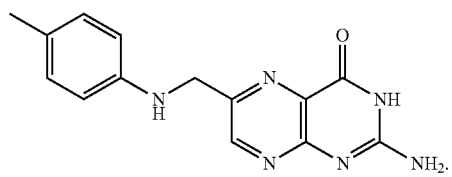

2. A pharmaceutical composition comprising the compound of claim 1 and at least one pharmaceutically acceptable carrier, excipient, or diluent.

3. A method for modulating folate receptor binding in a cell, wherein the method comprises contacting the cell with a therapeutically effective amount of the pharmaceutical composition of claim 2.

4. A method for reducing nephrotoxicity in a subject in need thereof, wherein the method comprises administering to the subject a therapeutically effective amount of the pharmaceutical composition of claim 2.

5. The method of claim 4, wherein the nephrotoxicity is cisplatin-induced.

6. The method of claim 4, wherein the nephrotoxicity is drug-induced.

7. A method for treating kidney disease in a subject in need thereof, wherein the method comprises administering to the subject a therapeutically effective amount of the pharmaceutical composition of claim 2.

8. A compound having the formula:

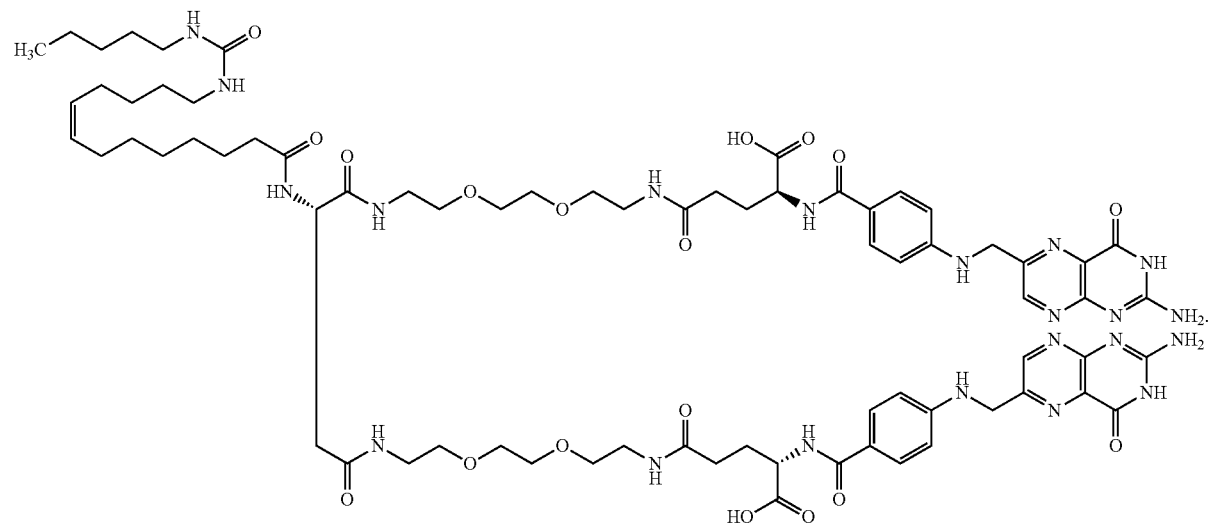 [SMILES: CCCCCNC(=O)NCCCC/C=C\CCCCCCC(=O)N[C@@H](CC(=O)NCCOCCOCCNC(=O)CC[C@H](NC(=O)c1ccc(NCc2cnc3nc(N)[nH]c(=O)c3n2)cc1)C(=O)O)C(=O)NCCOCCOCCNC(=O)CC[C@H](NC(=O)c1ccc(NCc2cnc3nc(N)[nH]c(=O)c3n2)cc1)C(=O)O]

9. A pharmaceutical composition comprising the compound of claim 8 and at least one pharmaceutically acceptable carrier, excipient, or diluent.

\* \* \* \* \*